United States Patent [19]
Allen et al.

[11] Patent Number: 5,416,000
[45] Date of Patent: * May 16, 1995

[54] ANALYTE IMMUNOASSAY IN SELF-CONTAINED APPARATUS

[75] Inventors: Michael P. Allen, Sunnyvale; Prithipal Singh, Los Altos, both of Calif.

[73] Assignee: Chemtrak, Inc., Sunnyvale, Calif.

[*] Notice: The portion of the term of this patent subsequent to Mar. 12, 2008 has been disclaimed.

[21] Appl. No.: 795,754

[22] Filed: Nov. 21, 1991

Related U.S. Application Data

[63] Continuation-in-part of Ser. No. 789,059, Nov. 7, 1991, abandoned, which is a continuation of Ser. No. 474,991, Feb. 6, 1990, Pat. No. 5,132,086, which is a continuation of Ser. No. 353,910, May 18, 1989, Pat. No. 4,959,324, and a continuation-in-part of Ser. No. 357,045, May 24, 1989, abandoned, which is a continuation-in-part of Ser. No. 324,407, Mar. 16, 1989, Pat. No. 4,987,085, which is a continuation-in-part of Ser. No. 195,881, May 19, 1988, Pat. No. 4,999,287, and a continuation-in-part of Ser. No. 64,883, Jun. 22, 1987, Pat. No. 4,973,549.

[51] Int. Cl.⁶ .................. G01N 33/543; G01N 33/558

[52] U.S. Cl. ..................... 435/7.92; 422/56; 422/58; 435/7.9; 435/7.93; 435/7.94; 435/810; 435/970; 436/164; 436/169; 436/510; 436/514; 436/518; 436/530; 436/805; 436/810; 436/818; 436/824

[58] Field of Search ..................... 422/56-58, 422/61; 436/514, 518, 530, 510, 161, 162, 164, 169, 805, 810, 818, 824; 435/7.9, 810, 970, 7.92, 7.93, 7.94

[56] References Cited

U.S. PATENT DOCUMENTS 4,624,929  11/1986  Ullman ............................. 422/56
4,999,287  3/1991  Allen et al. ...................... 422/56

*Primary Examiner*—Toni R. Scheiner
*Assistant Examiner*—Christopher L. Chin
*Attorney, Agent, or Firm*—Bertram I. Rowland

[57] ABSTRACT

Methods and devices are provided for carrying out assays with minimal technical training where quantitative visual determinations may be made. The devices provide for a flow-path where a sample receiving element is moved from a sample receiving position to a position where it serves to bridge a transport element and a measurement element, so that the sample may be transported from the sample element to the measurement region. Labelled conjugates are provided which migrate a distance into the measurement region related to the amount of analyte in the sample.

16 Claims, 1 Drawing Sheet

U.S. Patent    May 16, 1995    5,416,000
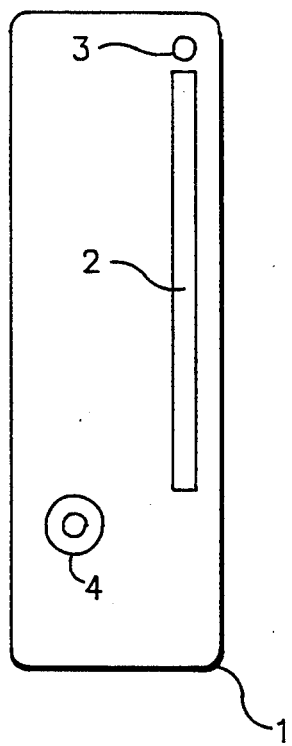
FIG.−1
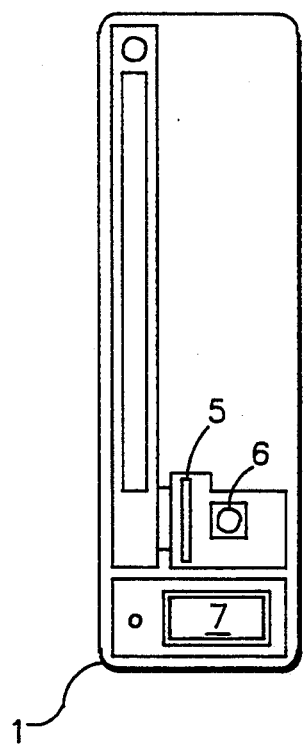
FIG.−2
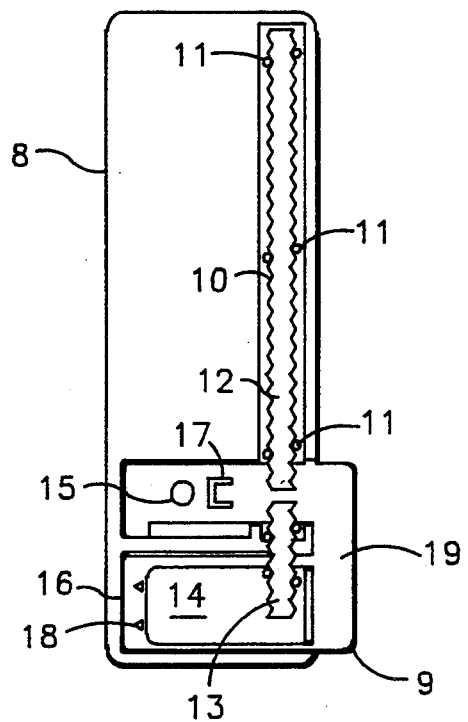
FIG.−3

ANALYTE IMMUNOASSAY IN SELF-CONTAINED APPARATUS

CROSS-REFERENCE TO RELATED APPLICATIONS

This application is a continuation-in-part of application Ser. No. 07/789,059 filed Nov. 7, 1991, now abandoned which is a continuation of application Ser. No. 07/474,991, filed Feb. 6, 1990, now U.S. Pat. No. 5,132,086 which is a continuation of application Ser. No. 07/353,910 filed May 18, 1989, now U.S. Pat. No. 4,959,324 and this application is a continuation-in-part of application Ser. No. 07/357,045, filed May 24, 1989, now abandoned which is a continuation-in-part of application Ser. No. 07/324,407, filed Mar. 16, 1989, now U.S. Pat. No. 4,987,085, which is a continuation-in-part of 07/195,881, filed May 19, 1988, now U.S. Pat. No. 4,999,287 and a continuation-in-part of application Ser. No. 07/064,883, filed Jun. 22, 1987, now U.S. Pat. No. 4,973,549.

INTRODUCTION

1. Technical Field

The field of this invention relates to analyte immunoassays.

2. Background

With the increasing availability of drugs for the treatment of a variety of diseases, the identification of a wide variety of compounds associated with particular pathogens, and the need to detect small amounts of contaminants in a wide variety of natural fluids in the environment or in processing plant effluents, there has been a concomitant expansion in methods for measuring analytes. For the most part, the measurement of analytes has occurred in clinical laboratories, where skilled technicians are able to perform a diversity of measurements with sophisticated equipment and reagents. However, there has been an ever greater need to allow for untrained people to perform assays, in doctors' offices, in the home, and in counseling clinics.

For assays to be carried out outside of clinical laboratories, it is desirable that the equipment, if any, required to read the results is simple and inexpensive, that a minimum number of reagents must be mixed and measured, that the sample be either easily measured or there be no requirement for measurement, that the protocol involve as few steps as possible and the assay be relatively insensitive to changes in the environment and actions of the operator. In addition, any device should be sturdy, relatively small, and have few, if any, moving parts. There is, therefore, substantial interest in developing assays which allow for non-technical people to obtain reproducible results without requiring sophisticated equipment to determine the assay value.

RELEVANT LITERATURE

U.S. Pat. No. 4,959,324 describes an apparatus which is self-contained for detecting analytes which serve as enzyme substrates. Other patents of interest include: U.S. Pat. Nos. 4,987,085 and 4,999,287, as well as the references contained in the aforementioned patents.

SUMMARY OF THE INVENTION

Methods and apparatus are provided for performing immunoassays for the determination of analytes, where the apparatus employs a continuous flow-path having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region has bound to it a member of a specific binding pair, complementary to the analyte. In addition, a conjugate of an enzyme with a member of the specific binding pair related to the analyte is employed as a reagent. By appropriate choice of reagents and protocols, the height of a signal can be related to the amount of an analyte in a sample.

BRIEF DESCRIPTIONS OF THE DRAWINGS

FIG. 1 is a diagrammatic plan view of a plate which covers the base plate; and

FIG. 2 is a diagrammatic plan view of the underside of of the cover plate.

FIG. 3 is a diagrammatic plan view of the base plate and slide of a device according to the subject invention;

DESCRIPTION OF SPECIFIC EMBODIMENTS

Methods and apparatus are provided for performing immunoassays in a self-contained apparatus. The apparatus comprises a flow path which is interrupted prior to receiving the sample, but becomes continuous after receiving the sample, reagents bound to a bibulous support, a source of an eluent for initiating the assay, and means for bringing the sample receiving element from a position in which it is out of liquid transfer relationship with the other members of the flow path to a position where it is in liquid transfer relationship with the other members of the flow path. The flow path is primarily divided into three parts:

(1) a bibulous short element which serves by capillary action to wick transport reagent solution to the sample receiving element; the sample receiving element; and the measuring region, where the downstream portion of the measuring region may serve a plurality of functions, serving to provide a threshold value by removing a predetermined amount of a reagent, allowing for mixing, providing a source of reagent(s) or the like. The flow path will be comprised for the most part of a bibulous material which absorbs a hydrophilic liquid and allows for transport of the reagents contained in the reagent solution, without chromatographing the components of the reagent solution to a significant extent.

The sample receiving element will normally serve a plurality of functions. The sample receiving element will receive the sample, serve as a bridge for transport of fluid between adjacent elements of the flow path, serve to measure the volume of the sample, and in certain instances may include one or more reagents which may affect the observed signal. The sample receiving element prior to initiation of the assay will be prevented from acting as a bridging element between adjacent members of the flow path and at or subsequent to initiation of the assay will serve as such bridging element. After receiving the sample, the sample receiving element is acted upon so as to become a bridging element in the flow path, the action normally involving movement of the sample receiving element from a position where it is out of fluid transport relationship to a position where it is in fluid transport relationship with the adjacent members of the flow path.

The measuring element will be an extended member, which allows for flow of the reagent solution through the measuring element by means of capillary action. The measuring element will have one or more members of a signal-producing system present on the measuring element, where the height or distance of the signal border e.g. a distance from the sample receiving element to the signal front, will be related to the amount of analyte in the sample and on the sample receiving member. By appropriate choice of members of the signal producing system for a quantitative assay, visually observable fronts may be obtained involving color in the visible region, fluorescent signals, or the like. In addition, the measuring element may have one or more additional regions between the measuring region and the sample receiving element. These regions may serve to control the dynamic range of the assay, to provide a delay before the elements of a signal producing system move into the measuring region, to allow mixing or a reaction to occur, and the like. By providing for a reaction in this region with a member of the signal producing system, the dynamic range of the assay will be changed in the measuring region. Since for many analytes there may be a threshold value which may be of interest and values below the threshold value are not of interest, one may provide a sufficient amount of reagent in a threshold contact region to react with a member of a signal producing system, so that the threshold value becomes a zero or low value observed in the measuring region. The reaction may be as a result of specific binding pair member complex formation, for example, with analyte, or the like. The mixing region will usually be a bibulous member which, serves to transport the liquid medium from the sample receiving element to the measuring zone or threshold zone.

Various techniques may be employed for inhibiting fluid flow to and from the sample receiving element to the other element involved in the flow path. Of particular interest is the use of a slide which can be moved from a first position, where the sample receiving element receives the sample, to a second position where the sample receiving element serves as a bridge between the adjacent members of the flow path. The slide prevents sample spreading to the other elements of the flow path, before it is time to carry out the assay.

The path of the sample receiving element moving from the site at which the sample is received to the site where it is in the flow path, may provide means for removing excess sample from the sample receiving element. Such means provide for a quantitative measure of the amount of sample received by the sample receiving element. Thus, by having a region in the path of the slide which is narrowed, so as to remove unabsorbed sample medium, without significantly squeezing the sample receiving element, the amount of sample absorbed by the sample receiving element may be relatively accurately reproduced. The narrowing may be as a result of a convexity, such as a rod in relief, a roller or any other convenient scraping means. The narrowing of the path should provide a space about equal to or slightly less than the wet thickness of the sample receiving element. The slide, therefore, not only serves to move the sample receiving element, but also to meter the amount of fluid absorbed by the sample receiving element.

The slide may also serve an additional function in releasing the transport or reagent solution. In providing for a self-contained device, the solution may be packaged in a sealed container, e.g. a scorable pouch, where the pouch may be situated in a chamber, where the chamber is situated in the device above a well for receiving the solution. The slide is provided with an arm which has protruding means, e.g. teeth, which can score or rip the seal of the pouch to release the solution. Instead of a pouch, one may provide for a foil which closes the bottom of the chamber, which foil may be scored or ripped to open. It is found that with an undesirable frequency, the solution in the chamber is not released when the seal is scored.

Methods for increasing the efficiency of release include providing a bibulous strip with a tongue extending from the scoring arm to the well region adjacent the transport element which extends into the well, where upon movement of the scoring arm, the strip moves into the chamber and initiates flow. Alternatively, one can provide for a path for the scoring arm, where the scoring arm undergoes a rapid drop after having scored a substantial portion of the length of the seal, where the sudden shock results in solution flow. Thus, with movement of the slide, one may move the sample receiving element, monitor the amount of sample associated with a sample receiving element, and release the transport or reagent solution for development of the assay.

The subject method and device may be employed in any situation where a fixed amount of a substance is involved, which can be transferred to the sample receiving element for measurement and ultimately an interaction occurs with another compound to produce a detectable boundary. These assays will be heterogeneous assays involving a solid support, such as ELISA assays, fluorescence assays, sandwich assays, and the like. The assays may involve any convenient label which will allow for a sharply differentiated boundary. The labels may include enzymes, particles, fluorescers, chemiluminescers, polymeric dyes, or other agent which will allow for a detectable boundary, particularly a visual detectable boundary.

For the most part, the assays will involve either a competition between the analyte and a conjugate of the label and a moiety capable of competing with the analyte for a complementary specific binding pair member or where the analyte acts as a bridge between two complementary specific binding pair members, one bound to the measurement region of the measuring element and the other complementary specific binding pair member dispersed in the reagent solution. The dispersed complementary binding pair member would be a labelled conjugate or in some protocols may serve as a member of a second specific binding pair, where the complementary member is the labelled conjugate.

Any analyte may be determined in accordance with the subject device and methodology. The analytes may be drugs, proteins, sugars, lipids, pollutants, contaminants, nucleic acids, or the like, naturally occurring or synthetic, monomeric or polymeric, individual molecules or aggregates, or the like. A long list of analytes, which is not intended to be exhaustive, may be found in U.S. Pat. No. 4,366,241.

Where an enzyme is used as a label, the final step of the assay will be the production of a detectable product. Therefore, substrates will have to be provided to the enzyme. The substrate may be provided in a number of ways. Conveniently, the measurement region may be flooded, immersed, or otherwise subjected to a solution comprising substrate, whereby the substrate solution is relatively evenly distributed over the measurement region. Alternatively, one may provide for a substrate solution as part of the self-contained device, where a container is provided which can be released by any convenient mechanism. For example, a chamber may be provided at one end of the device, where the substrate solution is contained in a sealed container which may be opened by any convenient means and can be transported by capillary action, flow or other channel to the measurement region. A more sophisticated situation would allow for scoring of the container containing the substrate solution at about the same time as the scoring occurs of the transport solution, and by providing an independent path to the measurement region, where the substrate solution will arrive at the measurement region after the transport solution.

Where blood is the sample, the sample receiving element may be positioned under a red blood cell removing filtering device. The blood sample will normally be one or a series of small drops, generally having a total volume under about 100 $\mu$L more usually from about 10 to 50 $\mu$L. The layers through which the sample flows will usually include a mesh layer, a first membrane, and a second membrane cooperating with the first membrane to insure the substantially complete removal of any interfering cells from the blood sample. The first layer of the separation member is used to reduce the concentration of red and white blood cells received by the second filtration member. Since the first membrane acts as a coarse separation means, the first membrane may take any of a wide variety of forms.

Various packings or sieving depth filters may be employed, such as glass fibers, cellulose or glass filters treated with red blood cell capture reagents, glass fiber filters, synthetic fiber filters or a composite material including any combination of the above materials. Glass fiber filters are available from such manufacturers as Whatman, Schleicher & Schuell, MSI, and Pall. The glass fiber filters are further characterized by a glass fiber diameter in the range of about 0.05-9$\mu$ and a density of about 50-150 g/m$^2$. The glass fiber filters may be illustrated by S & S Glass 30, Whatman GFD, and S & S 3662. The second membrane, when present, will be in fluid receiving relationship with the first membrane, and have an average porosity in the range of about 0.2$\mu$ to 7$\mu$, preferably about 1-5$\mu$, where the pores may or may not be of substantially uniform diameter through the membrane. When an asymmetric membrane is employed, desirably the membrane will have a minimum porosity not less than about 0.2$\mu$, preferably not less than about 0.45$\mu$ and a maximum porosity not greater than about 40$\mu$, usually not greater than about 20$\mu$. Illustrative microporous membranes include Filtrite polysulfone asymmetric, 20$\mu$-0.45$\mu$, Sartorious cellulose acetate 1.2$\mu$, Nucleopore 0.4-5 $\mu$m polycarbonate, etc.

The sample receiving element will be immediately beneath the red blood cell removing membrane(s) and in fluid receiving relationship with the membrane(s). The sample receiving element will normally be a bibulous member able to absorb a sample fluid and will usually include cellulosic materials, e.g. paper, or the like. A sample receiving element will usually be of a size in the range of about 5 to 50 mm$^2$ surface area and a thickness in the range of about 0.1 to 2 mm, having a volume capacity in the range of about 1-30 $\mu$L.

The sample may be any convenient sample, which includes physiologic fluids, e.g. blood, plasma, urine, cerebrospinal fluid, ocular lens fluid, etc., waste streams, effluents, soil, water sources, foods, etc.

The measurement region will have non-diffusively bound a member of a specific binding pair. The specific binding pairs comprise a ligand and a receptor, where the ligand may be any compound to which a complementary member binds. Normally, the ligand will be an organic molecule, which may be naturally occurring or synthetic. The receptor may be any of a wide variety of receptors, where they may be naturally occurring and bind to a specific ligand or may be as a result of immunization, where an antibody is produced which binds specifically to an epitopic site of the ligand. The specific binding pair member which is bound to the measurement region element may be either the ligand or receptor, depending upon the analyte to be measured. Various techniques may be used to non-diffusively bind the specific binding pair member to the measurement region element, either covalently or non-covalently.

Papers are available which are activated and will react directly with a wide variety of functional groups or functionalized papers are available where the functional groups may be activated or will react with an active group present on the specific binding pair member. Thus, one may have such functionalities as amino groups, carboxy groups, carbonyl groups, thiol groups, olefins, and the like. One may have reactions between carboxylic acid groups and the amines to form amides, amines and carbonyl groups under reducing conditions to have form alkylamines, thiols and disulphides to have thiol exchange, thiols and olefins to form thioethers, etc. The specific binding pair member will be dispersed through the measurement region in a predetermined manner, uniformly or graduated or other pattern as appropriate. By having an accompanying scale the position of the border may be interpreted in relation to the amount of analyte in the sample.

The materials used for the flow-path elements may be any bibulous material, usually having a thickness in the range of about 0.05 to 2 mm, more usually 0.15 to 0.75 mm. A wide variety of bibulous supports may be employed, particularly cellulosic supports, such as chromatography paper, silica on a support, alumina on a support, polymeric membranes such as nitrocellulose and nylon, etc. The characteristics of the bibulous material employed for the measurement region may include the need for covalent bonding, irreversible binding of the detectable label, development of a clear and sharp border, and a convenient flow rate.

The entire flow-path may have a length of about 25 to 200 mm, more usually from about 50-150 mm, preferably about 100 mm. About 25% to 90% of the length of the flow path will be the measurement region, comprising a quantitation zone, optionally a mixing zone and/or threshold value zone. The mixing and/or threshold value zone will generally be a total of about from 5% to 35% of the flow-path. The transport element will generally be from about 5-25 mm, being about 10% to 20% of the flow-path. A sample receiving element will generally be from about 1-10% of the flow path. The width of the strips may be varied widely, usually being at least 2 mm and not more than about 10 mm, preferably from about 3-7 min. The two strips will usually each overlap the sample receiving element by at least about 0.2 mm and not more than about 2 mm, usually about 1 mm, being primarily a matter of convenience.

For further understanding of the invention, the drawings will now be considered.

In FIG. 1, a top view of cover plate 1 is shown, where viewing window for slot 2 allows one to view the measuring region, while indicator hole 3 indicates when the transport solution has completely traversed the measurement region. An orifice 4 is provided for introduction of the sample. In FIG. 2, a bottom view of cover plate 1 is shown, where squeegee metering bar 5 for removing excess fluid from the sample receiving element is present adjacent orifice 6 which communicates with orifice 4 and holds the filters or membranes for separating the cells from blood samples. A chamber 7 is provided for holding the transport solution.

In FIG. 3, a top view of the base plate is provided with slide 9. A slot 10 is present for receiving the measurement strip 12. Slot 10 provides locating pins 11 for orienting the measurement strip, where the edges of the measurement strip are serrated to improve the sharpness of the border. Wicking strip 13 extends into well 14 which receives the transport solution which is contained in chamber 7. Slide 9 has two arms, one arm having opening 15 for receiving the sample receiving element and the other arm 16 which has protruding teeth 18 for scoring a sealing foil enclosing the transport solution in chamber 7. By moving slide handle 19 away from base plate 8, the sample receiving element in hole 15 is moved into a position between strips 12 and 13 to act as a bridge for the transport solution, while scoring teeth 18 open the transport solution container in chamber 7 so that the solution may flow into well 14 and be wicked by transport element 13. A snap 17 for locking the slide in place is provided, so that once the slide is extended it cannot be returned to its initial position.

The following examples are offered by way of illustration and not by way of limitation.

EXPERIMENTAL

Example 1—Theophylline Assay using Commercially Available Strip.

The immunochromatographic strip from a theophylline Acculevel ® device was removed from the plastic cassette. The strip was affixed to a 10 mil acetate plastic backing with 3M 415 double stick adhesive tape so that the dye band on top of the strip faced upwards and the top of the strip was flush with the end of the plastic backing. At the lower end of the strip, an 11×5 mm section of S&S 470 paper to serve as a mixing zone was positioned on the backing to provide a 1 mm overlap with the bottom of the strip and a 1 mm overlap with a 7×5 mm section of Whatman 31ET paper also adhered to the backing to serve as a sample site. An additional 11×5 mm section of S&S 470 paper was adhered below the 31 ET paper with a 1 mm overlap to the 31ET paper and ending at the terminus of the plastic backing. To interrupt wicking between the 31 ET paper and the two 470 sections, 3×10 mm pieces of Mylar were positioned between the 1 mm overlap points (The Acculevel ® control solution was diluted 1:10 with pH 7.0 phosphate buffer. Solutions of 0.5 μg/mL and 1.0 μg/mL theophylline in phosphate buffer were gravimetrically prepared.) The samples were applied to the 31ET paper section of the strip with a micropipet. In all cases, 10 μl of sample was applied. After application of the sample, the Mylar pieces were removed and the strips placed in the Acculevel ® wicking buffer (solution 1) with the lower 470 section dipped in the solution. The solution wicked through the lower 470 section, through the 31ET paper (sample site), through the mixing zone, and finally through the immunochromatographic strip. The wicking was allowed to continue until the dye level at the top of the strip smeared.

Immediately after completion of the wicking, the strip was removed from the wicking solution and the immunochromatographic paper was immersed in Acculevel ® developer (solution 2). A color band of good quality and rocket front developed over several minutes. When the color development was complete, the strip was removed from the developer and the migration height of the color band was measured from the bottom of the strip to the color band front (apex).

| RESULTS | MIGRATION HEIGHT |
| --- | --- |
| 1/10 Acculevel ® control 2.90 μg/ml | 39 mm |
| .5 μg/mL theophylline solution | 33 mm |
| 1.0 μg/mL theophylline solution | 40 mm |

Creating a 2-point curve with the 0.5 and 1.0 μg/mL solutions allowed for interpolation of the 1:10 Acculevel ® control. A value of 0.9 μg/mL was indicated. This value falls within the control range 0.83–1.23 μg/ml.

Example 2—Immunochromatographic Assay for Theophylline

Materials:
Monoclonal antibodies against theophylline (cat #16202 and 16203, Synbiotics)
Sodium Sulfate (anhydrous)
Dialysis tubing and clips
0.1M Sodium Bicarbonate buffer pH 8.5
0.1M Phosphate buffered saline pH 7.0
1.0M Ethanolamine buffer pH 8.0
0.5% (w/v) Polyvinyl alcohol (PVA)
0.9% (w/v) Sodium Chloride
1,1'-Carbonyldiimidazole activated Whatman 31ET paper (CDI paper), lot 90A161
PD 10 columns (Pharmacia)
12 μm Nitrocellullose (S&S) laminated onto Mylar cards
Developing solution (4-Cl-l-naphthol/$H_2O_2$): 0.1M MOPSO pH 7.0 containing 4-Cl-l-naphthol (0.4 g), BSA (4.0 g), PVA (5.0 g), NaCl (0.9% w/v) and $H_2O_2$ (0.03%) per liter Preparation of Immunochromatographic Test Strips
a) Preparation of Immunoglobulin fraction:

To 5 ml of ascites fluid (Mab 16203) was slowly added 0.875 g of sodium sulfate with stirring. After complete dissolution, stirring was further continued for 30 minutes at room temperature. The suspension was centrifuged at 3000 rpm for 10 minutes and the pellet was re-suspended in 5 ml 0.9% NaCl solution. The precipitation was repeated and the pellet resuspended in 2.5 ml 0.1M sodium bicarbonate buffer pH 8.5. The sample was passed down a PD 10 column equilibrated with 0.1M sodium bicarbonate buffer, pH 8.5. One ml fractions were collected and fractions containing Immunoglobulin G (determined by A280 nm) were pooled and dialysed overnight against several changes of 0.1M sodium bicarbonate buffer, pH 8.5.

Immobilization of Antibody:
a) CDI activated Whatman 31 ET paper.
Monoclonal antibody was prepared at 1.0 g of IgG per liter in 0.1M sodium bicarbonate buffer (pH 8.5).
The antibody solution (25.0 ml) was poured into a glass dish (8"×11") tilted at 45°. Dried CDI-activated paper was slowly and uniformly passed through the solution by inserting one end in the liquid and pulling the paper through, then rotating and inverting the paper (180°) and repeating the process. The paper was then incubated in the antibody solution for 2 hours at room temperature or overnight at 4°C.

The paper was removed from the antibody solution and washed extensively with 0.1M PBS pH 7.0 (200 ml). Unreacted CDI sites on the paper were blocked by incubating the paper in 1.0M ethanolamine solution (100 ml), pH 8.0 for 2 hours at room temperature. The paper was then washed with 0.1M PBS, pH 7.0 (200 ml) followed by deionized water (50 ml). The paper was then immersed in 0.5% PVA solution (100 ml) for 50 minutes at room temperature. Finally the paper was dried at 45° C. and stored desiccated at 4° C. until required for use.

b) Nitrocellulose

Nitrocellulose (12.0 μm) laminated onto a mylar card was slowly and uniformly passed through 0.25 g/L antibody (IgG fraction) solution (25 ml) prepared in 0.1M sodium bicarbonate buffer (pH 8.5). The dipping process was similar to the procedure described for CDI activated paper except following the second dip the card was dried in an oven preheated to 45° C. for 15 minutes. The card was stored desiccated at 4° C. until required.

Lamination of Antibody Paper

Antibody paper was laminated onto a mylar card which consisted of a sample pad (5 mm) overlapped 1 mm by the wicking strip (12 mm) from below and the antibody paper (80 mm) from above. The card was then cut into 5 mm wide strips.

Two-step Assay for Theophylline

Briefly the assay configuration is composed of a laminated chromatography strip as described previously and a wicking reagent which is a buffered protein solution containing peroxidase-labeled theophylline (0.75 μg/ml).

In the first step, theophylline sample (2.5–40 g/ml) in plasma or buffer (2.5 μl or 1.0 μl) was deposited on the sample pad. Wicking was initiated by placing the lower portion of the wicking strip in contact with the wicking reagent (0.5 ml/test tube). The enzyme-labeled theophylline and sample were allowed to capillary migrate up the chromatography strip. The capillary migration was complete within 10 minutes.

The second step involved the development of color on the strips by transferring the strips to a test tube containing 10 ml of a substrate solution (4-Cl-1-naphthol/$H_2O_2$). The color was allowed to develop for 5 minutes. The strips were removed from the test tubes and migration heights measured (see Table 1).

The following table indicates the results:

TABLE 1

| | Migration height as a function of Theophylline concentration using a sample size of 1.0 μL. | |
|---|---|---|
| | Theophylline (μg/mL) | Migration height (mm) |
| 1 | 2.5 | 9.0 |
| 2 | 5 | 15.0 |
| 3 | 10 | 26.0 |
| 4 | 20 | 42.0 |
| 5 | 40 | 52.0 |

EXAMPLE 3

Highly Sensitive Immunochromatographic Assay

A two-step assay was used to demonstrate a highly sensitive immunochromatographic assay. Antibody immobilized to laminated nitrocellulose was used as the measuring strip. The assay configuration was composed of assay strips (80×5 mm; measuring strip, sample pad and wicking strip) and a wicking reagent.

In the first step, theophylline samples (5 μl) were deposited onto the sample pads. Wicking was initiated by placing the lower portion of the assay strips in wicking reagent (0.5 ml/test tube). Following capillary migration the strips were removed and transferred to test tubes containing substrate solution (10 ml). Color on the strips were developed for 5 minutes and then the strips were removed and migration heights measured from the bottom of the measuring strip to the color band front (See Table 2).

TABLE 2

| | Migration height as a function of Theophylline concentration. | |
|---|---|---|
| | Theophylline (μg/mL) | Migration height (mm) |
| 1 | 1.500 | 5.0 |
| 2 | 3.100 | 7.0 |
| 3 | 6.250 | 10.0 |
| 4 | 12.500 | 14.0 |
| 5 | 25.000 | 17.0 |

EXAMPLE 4

Theophylline Assay in Cassettes

Theophylline calibrators (1.25, 2.5, 5.0 and 10 μg/mL) were prepared in either theophylline free plasma or in 0.055 mol/L Tris/HCl buffer pH 8.0 containing 70 mg/ml BSA.

Cassettes (illustrated in FIGS. 1–3) were assembled with measuring strips immobilized with antibody to theophylline. The cassettes were used for this study. To the sample site was applied theophylline calibrators (40 μl), after waiting two minutes the slide was pulled and wicking initiated. Following completion of wicking (as seen by dye in the complete window), substrate solution was applied to the measurement strip through the viewing window using a Pasteur pipette. The color was developed for 5 minutes and then the migration height was measured off the scale on the cassette. The entire assay was complete within 15 minutes. (See Table 3).

TABLE 3

| | Migration height as a function of theophylline concentration in the presence or absence of plasma. Study performed in Accumeter ™ cassettes. | | |
|---|---|---|---|
| | Theophylline (μg/mL) | Buffer (mm) | Plasma (mm) |
| 1 | 1.250 | 16.0 | 21.5 |
| 2 | 2.500 | 25.0 | 33.0 |
| 3 | 5.000 | 42.0 | 44.0 |
| 4 | 10.000 | 53.0 | 53.0 |

EXAMPLE 5

Human Chorionic Gonadotropin (HCG) Assay

To demonstrate the detection of the presence of HCG, the chromatography strip from the Clear Blue Easy Device (Unipath Limited; Bedford, UK) was placed in the cassette described above. The strip has a zone proximal to one end which is dipped into the sample which contains anti-α-HCG-blue latex bead conjugate, diffusively bound to the strip. Distal from the latex beads in the direction of flow of the buffer is a test zone containing anti-β-subunit HCG, followed by a control zone comprising anti-(anti-HCG), both of the antibody compositions being non-diffusively bound in their respective zones. This assay is a sandwich-type immunoconcentration format using colored latex beads as a signal reagent. A negative urine will wick up the strip and no binding of the anti-α-HCG conjugate will occur. This conjugate will therefore not bind to the test zone, but will bind to the control zone. The negative results will be seen as a blue line only in the control zone. A urine positive for HCG at or above 50 mU/ml will result in the binding of the anti-α-HCG-bead conjugate to the HCG in the sample. This species will then migrate to the test zone and the anti-β-HCG subunit antibody will bind the β-subunit thereby forming a sandwich and immobilizing the colored bead in the test zone. All unbound antibody-bead conjugates move to the control zone to give a positive control response. In a positive sample, both test and control zones are colored.

The Clear Blue Easy strip, approximately 4 cm long was inserted into the cassette and Whatman 31ET paper used as the wick, where the wick extended from the sample receiving port to the Clear Blue Easy chromatography strip.

In the tests carried out, 1 ml of urine from a pregnant woman was added at the sample site and allowed to wick to the chromatography component. A clearly positive reaction was obtained, where both the test and control zones were colored.

EXAMPLE 6

Digoxin Assay

Following the procedure described in Example 4, an assay was carried out for digoxin. The chromatography strip for the measurement zone was immersed in a solution of anti-digoxin monoclonal antibody in PBS buffer, pH 7.0 at 0.05 mg/ml. 10 μl samples were employed at varying concentrations and the results plotted to provide a smooth curve varying from 1 ng/ml to 20 ng/ml. The following table indicates the results.

TABLE 4

| | Digoxin ng/mL | Migration height (mm) |
| --- | --- | --- |
| 1 | 1.000 | 7.000 |
| 2 | 2.500 | 11.000 |
| 3 | 5.000 | 16.000 |
| 4 | 10.000 | 21.000 |
| 5 | 20.000 | 33.000 |

It is evident from the above results, that a simple, accurate method is provided for quantitatively determining a wide variety of analytes. Minimum operator involvement is required, and low technical skills are permissible. The assay is substantially free of response-interfering agents and conditions, so that it is highly reliable, providing accurate results at low concentrations of analyte. The subject device and assays can therefore find use in environments where untrained people wish to carry out determinations for therapeutic dosage monitoring, in the field, for counseling or monitoring various physiological states, such as cholesterol levels, glucose levels, and the like.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or Scope of the appended claims.

What is claimed is:

1. A method for detecting the presence of an analyte in a sample, wherein said analyte is a member of a specific binding pair, employing a signal producing system having a reagent bound non-diffusibly to a surface and at least one reagent free in solution, said signal producing system with said analyte producing a detectable signal in a signal measurement region on a measuring strip as a said surface, wherein a complementary member of said signal producing system specific for said analyte is said reagent non-diffusibly bound to said surface and a solution comprising a labelled detecting member of said signal producing system is provided, wherein said labelled detecting member binds to said analyte or said complementary member bound non-diffusibly to said surface, said method comprising:

applying said sample to a sample receiving element;

bringing said sample receiving element into fluid transfer relationship with a transfer strip and said measuring strip;

flowing transport solution through said transfer strip, sample receiving element and measurement region in the direction of flow, whereby any analyte in said sample is transported from said sample receiving element to said measurement region in conjunction with said labelled detecting member, wherein said labelled detecting member may be competitive with said analyte for said non-diffusibly bound complementary member or complementary to said analyte; and determining the distance said labelled detecting member bound to said surface has migrated in said measurement region as a measure of the amount of analyte in the sample.

2. A method according to claim 1, wherein said labelled detecting member is a conjugate of an enzyme and a moiety competitive with said analyte for said complementary member.

3. A method according to claim 1, wherein said labelled detecting member comprises a label attached to a specific binding pair member complementary to said analyte.

4. A method according to claim 1, wherein said labelled detecting member comprises an enzyme and said determining comprises:

contacting said measurement region with substrate for said enzyme and any remaining members of said signal producing system, wherein said substrate produces a visual product defining a border for determining said distance.

5. A method according to claim 4, wherein said visual product is produced by reaction of the enzyme catalyzed product with a compound non-diffusibly bound to said surface in said measurement region.

6. A method for detecting the presence of an analyte in a sample, wherein said analyte is a member of a specific binding pair, employing a signal producing system having a reagent bound non-diffusibly to a surface and at least one reagent free in solution, said signal producing system comprising a conjugate of an enzyme with a moiety that is capable of competing with said analyte for binding to a complementary member of said specific binding pair, said signal producing system producing a detectable signal in a signal measurement region on a measuring strip as a said surface, wherein a complementary member of said signal producing system specific for said analyte is said reagent non-diffusibly bound to said surface, said method comprising:
- applying said sample to a sample receiving element;
- bringing said sample receiving element into fluid transfer relationship with a transfer strip and said measuring strip;
- flowing transport solution through said transfer strip, sample receiving element and measurement region in the direction of flow, whereby any analyte in said sample is transported from said sample receiving element to said measurement region in conjunction with said conjugate;
- adding an enzyme substrate solution to said measurement region resulting in detectable product from reaction of said enzyme substrate with said enzyme; and
- determining the distance said detectable product is present in said measurement region as a measure of the amount of analyte in the sample.

7. A method according to claim 6, wherein said visual product is produced by reaction of the enzyme catalyzed product with a compound non-diffusibly bound to said surface in said measurement region.

8. A method according to claim 6, wherein said enzyme is a peroxidase and said transport medium comprises a peroxide.

9. A method according to claim 6, wherein said analyte is theophylline.

10. A method according to claim 6, wherein said analyte is digoxin.

11. A method for detecting the presence of a polyepitopic antigenic analyte in a sample, wherein said analyte is a member of a specific binding pair, employing a signal producing system having a reagent bound non-diffusibly to a surface and at least one reagent free in solution, said signal producing system comprising a conjugate of an enzyme with a moiety complementary to said analyte for binding to said analyte, said signal producing system producing a detectable signal in a signal measurement region on a measuring strip as a said surface, wherein a complementary member of said signal producing system specific for said analyte is said reagent non-diffusibly bound to said surface, said method comprising:
- applying said sample to a sample receiving element;
- bringing said sample receiving element into fluid transfer relationship with a transfer strip and said measuring strip;
- flowing transport solution through said transfer strip, sample receiving element and measurement region in the direction of flow, whereby any analyte in said sample is transported from said sample receiving element to said measurement region in conjunction with said conjugate;
- adding an enzyme substrate solution to said measurement region resulting in detectable product from reaction of said enzyme substrate with said enzyme; and
- determining the distance said detectable product is present in said measurement region as a measure of the amount of analyte in the sample.

12. A method according to claim 11, wherein said visual product is produced by reaction of the enzyme catalyzed product with a compound non-diffusibly bound to said surface in said measurement region.

13. A method according to claim 11, wherein said analyte is human chorionic gonadotropin.

14. A method for detecting the presence of an analyte in a sample, wherein said analyte is a member of a specific binding pair, employing a signal producing system having a reagent bound non-diffusibly to a surface and at least one reagent free in solution, said signal producing system with said analyte producing a detectable signal in a signal measurement region on a measuring strip as a said surface, wherein a complementary member of said signal producing system specific for said analyte is said reagent non-diffusibly bound to said surface and a solution comprising a labelled detecting member of said signal producing system is provided, wherein said labelled detecting member binds to said analyte or said complementary member bound non-diffusibly to said surface, said method comprising:
- applying said sample to a sample receiving element;
- bringing said sample receiving element into fluid transfer relationship with a transfer strip and said measuring strip, while at the same time releasing a transport solution to be absorbed by said transfer strip;
- flowing transport solution through said transfer strip, sample receiving element and measurement region in the direction of flow, whereby any analyte in said sample is transported from said sample receiving element to said measurement region in conjunction with said labelled detecting member, wherein said labelled detecting member may be competitive with said analyte for said non-diffusibly bound complementary member or complementary to said analyte; and
- determining the distance said labelled detecting member bound to said surface has migrated in said measurement region as a measure of the amount of analyte in the sample.

15. A method according to claim 14, Wherein said labelled detecting member is a conjugate of an enzyme and a moiety competitive with said analyte for said complementary member.

16. A method according to claim 14, wherein said labelled detecting member comprises a label attached to a specific binding pair member complementary to said analyte.

* * * * *